(12) United States Patent
Wang et al.

(10) Patent No.: US 9,781,724 B2
(45) Date of Patent: Oct. 3, 2017

(54) METHOD TO USE AUXILIARY CHANNEL TO ACHIEVE FAST AND POWER-EFFICIENT ASSOCIATION IN WIRELESS NETWORKS

(75) Inventors: Dong Wang, Ossining, NY (US); Monisha Ghosh, Chappaqua, NY (US); Delroy Smith, North Andover, MA (US); Hongqiang Zhai, Ossining, NY (US); Maulin Dahyabhai Patel, Tuckahoe, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 620 days.

(21) Appl. No.: 13/983,880

(22) PCT Filed: Feb. 3, 2012

(86) PCT No.: PCT/IB2012/050516
§ 371 (c)(1),
(2), (4) Date: Aug. 6, 2013

(87) PCT Pub. No.: WO2012/107866
PCT Pub. Date: Aug. 16, 2012

(65) Prior Publication Data
US 2013/0316652 A1 Nov. 28, 2013

Related U.S. Application Data

(60) Provisional application No. 61/440,889, filed on Feb. 9, 2011.

(51) Int. Cl.
*H04W 72/04* (2009.01)
*H04W 48/06* (2009.01)
(Continued)

(52) U.S. Cl.
CPC ......... *H04W 72/048* (2013.01); *H04W 48/06* (2013.01); *A61B 5/0024* (2013.01); *A61B 2560/0209* (2013.01); *H04W 84/18* (2013.01)

(58) Field of Classification Search
CPC combination set(s) only.
See application file for complete search history.

(56) References Cited

U.S. PATENT DOCUMENTS

| | | | |
|---|---|---|---|
| 7,457,620 B2 | 11/2008 | Lam et al. | |
| 2002/0089985 A1* | 7/2002 | Wahl | H04Q 11/0478 370/395.1 |

(Continued)

OTHER PUBLICATIONS

Phillips Healthcare System (Oct. 5, 2009).*
(Continued)

*Primary Examiner* — Cindy Trandai

(57) ABSTRACT

A medical system includes one or more MBAN devices that acquire and communicate patient data. The medical system further including one or more medical body area network (MBAN) systems, each MBAN system including the one or more MBAN devices that communicate the patient data with a hub device via short-range wireless communication, the communication of the patient data via the short-range wireless communication being within a predefined spectrum. The hub device receives patient data communicated from the one or more MBAN devices and communicates with a central monitoring station via a longer range communication. The one or more MBAN devices transmit an association request to the hub device on one or more auxiliary channels to associate each MBAN device with the MBAN system, the auxiliary channels being outside the predefined spectrum.

19 Claims, 5 Drawing Sheets

Figure 1:
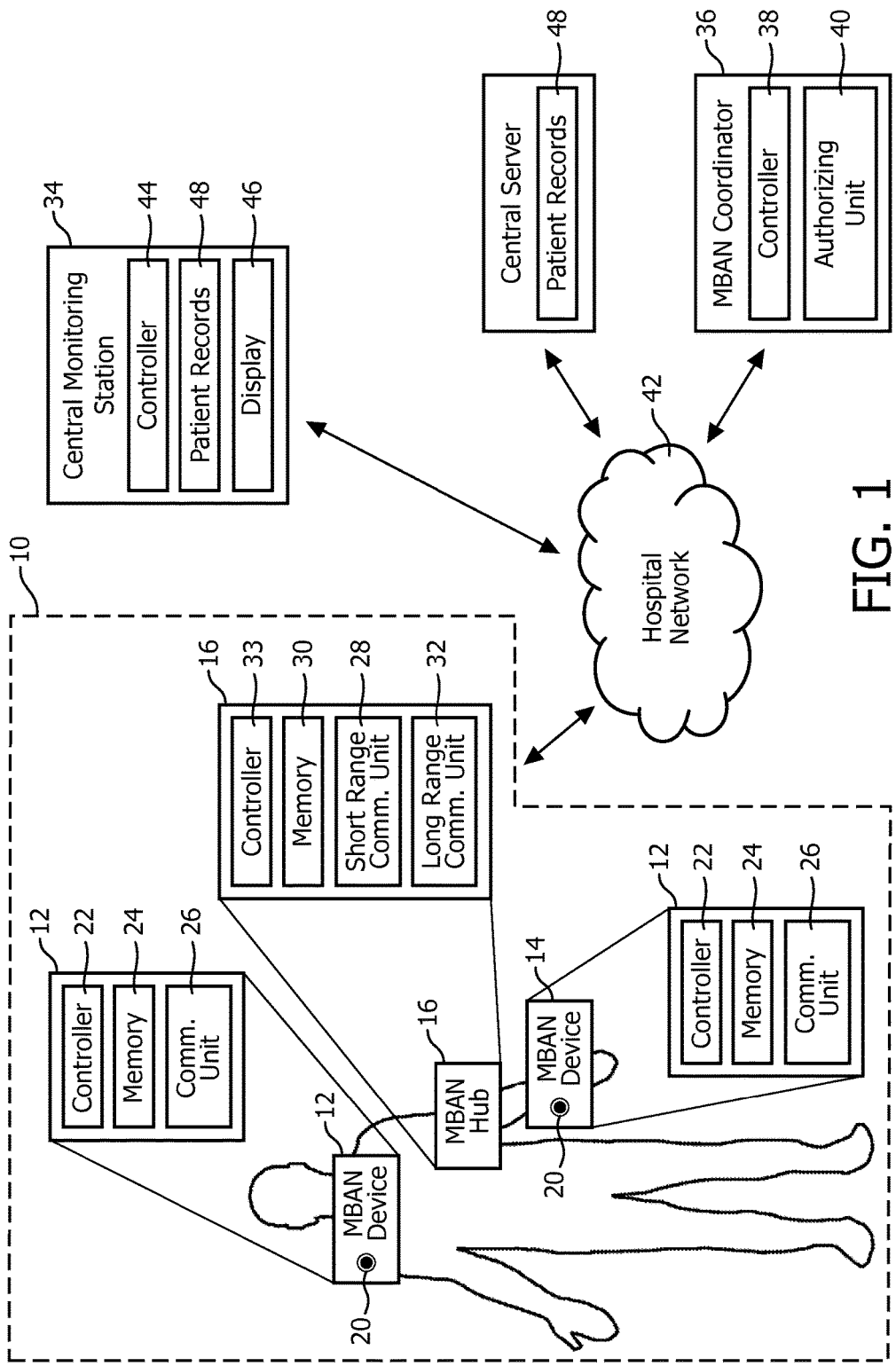

(51) Int. Cl.
    *H04W 84/18*    (2009.01)
    *A61B 5/00*     (2006.01)

(56) References Cited

U.S. PATENT DOCUMENTS

| | | |
|---|---|---|
| 2003/0203740 A1* | 10/2003 | Bahl et al. .................... 455/516 |
| 2005/0063334 A1 | 3/2005 | Fnu et al. |
| 2006/0251256 A1* | 11/2006 | Asokan ................. H04L 63/065 |
| | | 380/270 |
| 2007/0112962 A1 | 5/2007 | Lewontin |
| 2010/0075704 A1* | 3/2010 | McHenry et al. ............ 455/509 |
| 2010/0226342 A1* | 9/2010 | Colling et al. ................ 370/336 |
| 2010/0271959 A1 | 10/2010 | Qi et al. |
| 2010/0315225 A1* | 12/2010 | Teague .................... 340/539.12 |
| 2011/0228832 A1* | 9/2011 | De Francisco Martin ... 375/224 |
| 2012/0063397 A1* | 3/2012 | Abedi ............... H04W 72/1205 |
| | | 370/329 |

OTHER PUBLICATIONS

OK, J., et al.; Using Shared Beacon Channel for Fast Handoff in IEEE 802.11 Wireless Networks; 2007; IEEE 65th Vehicular Technology Conference; VTC2007; pp. 849-853.

Ergen, S. C.; Zigbee/IEEE 802.15A Summary; 2004; pp. 1-37. http://www.prism.uvsq.fr/mogue/SENSORS/Sensor%20%20Net/MAC%20pro/zigbee_802.15.4.pdf.

Smith, D.; Philips Healthcare Reply Comments; Amendment of the Commission's Rules to Provide Spectrum for the Operation of Medical Body Area Networks; 2009; pp. 1-50. http://fjallfoss.fcc.gov/ecfs/document/view?id=7020244837.

\* cited by examiner

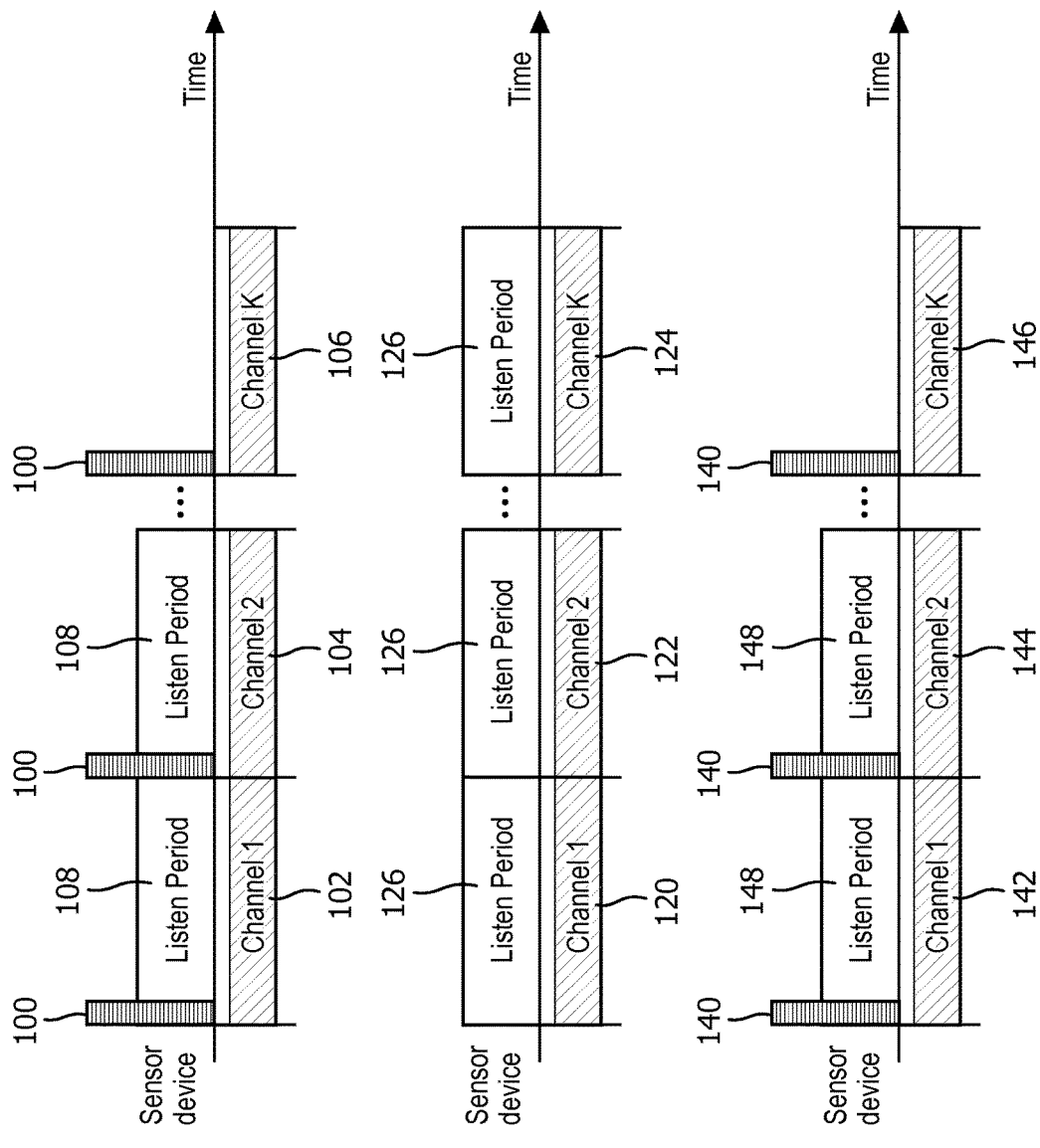

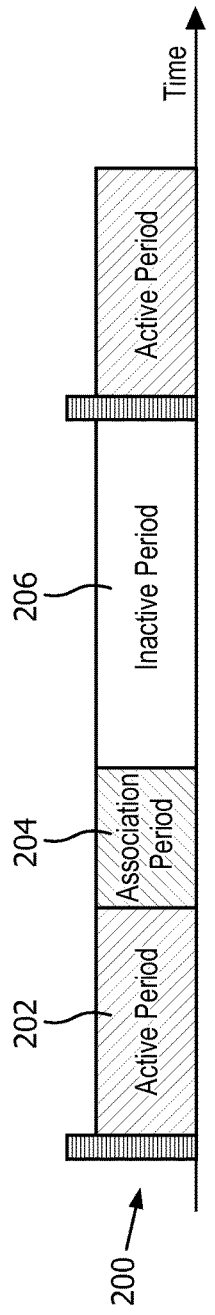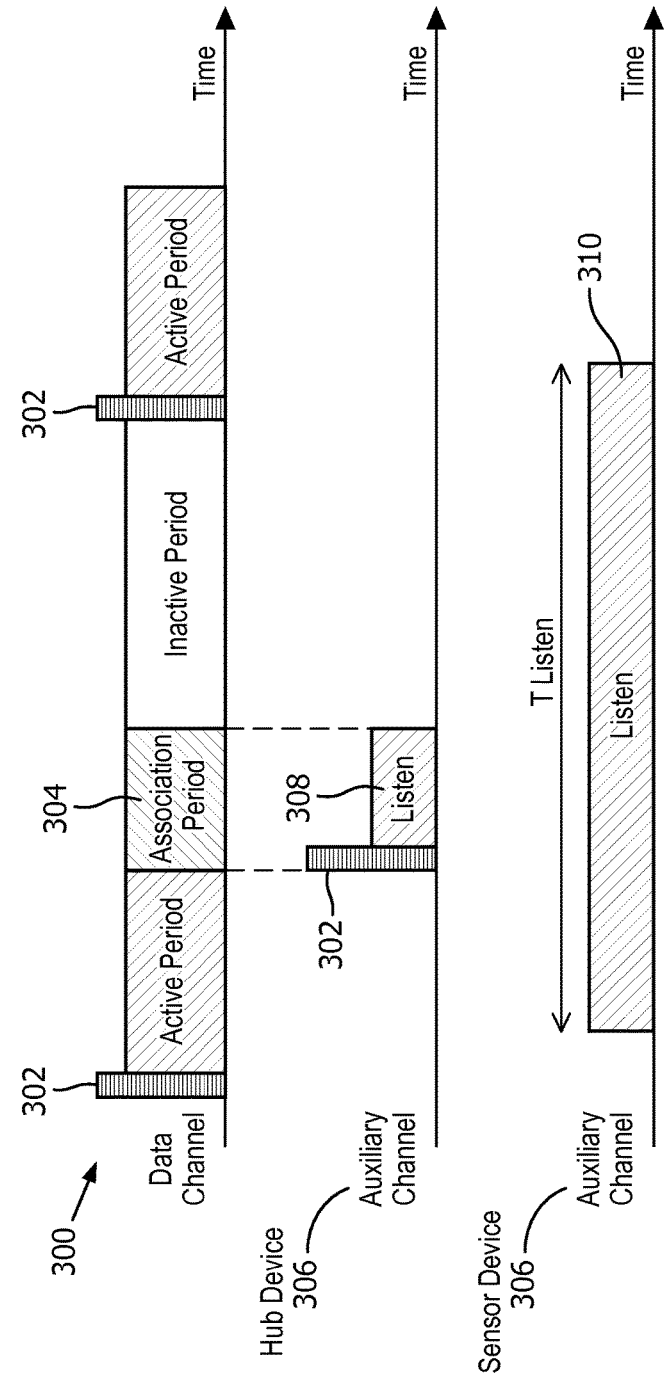

METHOD TO USE AUXILIARY CHANNEL TO ACHIEVE FAST AND POWER-EFFICIENT ASSOCIATION IN WIRELESS NETWORKS

CROSS REFERENCE TO RELATED APPLICATIONS

This application is a national filing of PCI application Serial No. PCT/IB2012/050516, filed Feb. 3, 2012, published as WO 2012/107866 A1 on Aug. 16, 2012, which claims the benefit of U.S. provisional application Ser. No. 61/440,889 filed Feb. 9, 2011, which is incorporated herein by reference.

The present application relates to medical monitoring and clinical data devices for monitoring the physiological condition of a patient. It finds particular application in the use of auxiliary channels to achieve fast and power-efficient association with wireless networks.

The rapid growth in physiological sensors, low power integrated circuits and wireless communication has enabled a new generation of medical body area networks (MBAN) to be used to monitor patients. MBANs provide low-cost wireless patient monitoring (PM) without the inconvenience and safety hazards posed by wired connections, which can trip medical personnel or can become detached so as to lose medical data. In the MBAN approach, multiple low cost sensors are attached at different locations on or around a patient, and these sensors take readings of patient physiological information such as patient temperature, pulse, blood glucose level, electrocardiographic (ECG) data, or so forth. The sensors are coordinated by at least one proximate hub or gateway device to form the MBAN. The hub or gateway device communicates with the sensors using embedded short-range wireless communication radios for example conforming with an IEEE 802.15.4 (Zigbee) short-range wireless communication protocol. Information collected by the sensors is transmitted to the hub or gateway device through the short-range wireless communication of the MBAN, thus eliminating the need for cables. The hub or gateway device communicates the collected patient data to a central patient monitoring (PM) station via a wired or wireless longer-range link for centralized processing, display and storage. The longer-range network may, for example, include wired Ethernet and/or a wireless protocol such as Wi-Fi or some proprietary wireless network protocol. The PM station may, for example, include an electronic patient record database, display devices located at a nurse's station or elsewhere in the medical facility, or so forth.

MBAN monitoring acquires patient physiological parameters. Depending upon the type of parameter and the state of the patient, the acquired data may range from important (for example, in the case of monitoring of a healthy patient undergoing a fitness regimen) to life critical (for example, in the case of a critically ill patient in an intensive care unit). Because of this there is a strict reliability requirement on the MBAN wireless links due to the medical content of the data. However, the current spectrum allocations and regulations for medical wireless connectivity do not meet the strict requirements of MBAN, including medical-grade link robustness, ultra low-power consumption and low-cost, due to either limited bandwidth or uncontrolled interference.

Short-range wireless communication networks, such as MBAN systems, tend to be susceptible to interference. The spatially distributed nature and typically ad hoc formation of short-range networks can lead to substantial spatial overlap of different short range networks. The number of short-range communication channels allocated for short range communication systems is also typically restricted by government regulation, network type, or other factors. The combination of overlapping short-range networks and limited spectral space (or number of channels) can result in collisions between transmissions of different short range networks. These networks can also be susceptible to radio frequency interference from other sources, including sources that are not similar to short-range network systems.

It is known to employ frequency spectrum regulation policies to increase the spectrum use efficiency. One trend is to allocate an MBAN spectrum specifically for MBAN applications and services as secondary users of the spectrum that has been previously allocated to other services on a primary basis. For example, it has been proposed in the U.S. to open the 2360-2400 MHz band (MBAN spectrum), currently assigned to others, to MBAN services as a secondary user. Similar proposals have been made or are expected to be made in other countries. The wide bandwidth, interference-free and good propagation properties of the MBAN spectrum would meet the strict requirements for medical-grade connectivity. In order to achieve co-existence between primary users and secondary users, some restrictions (or spectrum regulation rulings) would be put on the spectrum use of secondary users. One possible restriction could be to prohibit secondary users from transmission unless they are authorized by an assigned spectrum coordinator through some electronic ways. For example, an electronic key (E-Key) mechanism has been proposed as part of the technical rulings for the ongoing FCC Medical Body Area Network (MBAN) spectrum regulation.

In order to achieve this, the allocated MBAN spectrum would be used on a secondary basis meaning the MBAN systems would have to protect all the primary users in that spectrum and accept possible interference from those users. In order to protect the primary users, restrictions would need to be placed on the use of the MBAN spectrum. For example, the MBAN spectrum could only be used by MBAN devices within healthcare facilities outside predefined protection zones. If an MBAN device is outside the protection zone or does not have authorization from an E-key, the MBAN device could only transmit outside the MBAN spectrum. This means that an MBAN device can transmit within the MBAN spectrum only when it successfully gets authorization from an assigned MBAN coordinator.

In this proposed solution, a hospital planning to use the MBAN spectrum for MBAN services needs to register with the assigned MBAN coordinator. The MBAN coordinator will decide if it is feasible to use the MBAN spectrum through the coordination with the primary users and if yes, generate an E-Key to authorize the use of some or all of the MBAN spectrum for the registered hospital. All the MBAN devices by default are not allowed to transmit in the MBAN spectrum but can transmit outside the MBAN spectrum or other bands (e.g. 2.4 GHz ISM band). A registered healthcare facility will broadcast its E-Key, which is obtained from the MBAN coordinator, to all active MBAN systems within its facility (indoor). Once an MBAN hub device receives an E-Key from its registered healthcare facility, it will enable transmission within part or the entire of the MBAN spectrum authorized by the E-Key. The MBAN hub device is responsible for selecting a channel on which to operate and may notify its MBAN devices (or slave devices) via beacon transmission. Slave devices may not be allowed to transmit in the MBAN spectrum before they successfully associate with an MBAN system and maintained a connection with the MBAN hub device.

One of the important advantages of the MBAN spectrum is current commercial 2.4 G ISM band low power radio solutions, such as IEEE 802.15.4 and Bluetooth, can be reused in the MBAN spectrum. To associate with an MBAN system, an MBAN slave device has to acquire information about active MBAN systems nearby and select the desired MBAN system with which to associate. The MBAN device will then switch to the channel currently used by the selected MBAN system and send an association request to the hub device of the desired MBAN system. The hub device will determine whether such association is allowed and send its decision to the MBAN device via an association response. The MBAN device may transmit an acknowledgement frame to the hub device to complete the association procedure.

When an associated MBAN device loses its connection to the hub device, it may have to go through a similar procedure to rejoin its MBAN system. For example, in the IEEE 802.15.4 std., an orphaned device (i.e. a MBAN device that concludes that it lost connection to the MBAN system) may either reset its media access control (MAC) address and redo the association procedure or perform the orphaned device realignment procedure. In the orphaned device realignment procedure, the orphaned device will perform an orphan scan that allows it to attempt to relocate and reconnect to its hub device.

There are several problems which exist with the channel scan techniques used in the association or rejoin (i.e. orphaned device realignment) procedures. In order for a MBAN device to associate or rejoin an MBAN system, the MBAN device is required to actively transmit on a candidate channel before it successfully associates to a hub device. This might not be acceptable based on the restrictions of the MBAN spectrum. As mentioned above, it is likely that the restrictions would prohibit MBAN devices from transmitting in the MBAN spectrum before it gets authorization through the E-Key from its MBAN hub device. Moreover, during the association procedure and orphan realignment procedure, the MBAN device has to transmit association request/orphan notification frames before it successfully builds a connection to its hub device and its identification is verified by the hub device which it may not be allowed to do without having a valid E-key.

The present application provides a new and improved system and method for fast and power-efficient association with wireless networks which overcomes the above-referenced problems and others.

In accordance with one aspect, a medical system is provided. One or more MBAN devices acquire and communicate patient data. One or more medical body area network (MBAN) systems, each MBAN system including the one or more MBAN devices communicating the patient data with a hub device via short-range wireless communication, the communication of the patient data via the short-range wireless communication being within a predefined spectrum. The hub device receiving patient data communicated from the one or more MBAN devices and communicating with a central monitoring station via a longer range communication. The one or more MBAN devices transmitting an association request to the hub device on one or more auxiliary channels to associate each MBAN device with the MBAN system, the auxiliary channels being outside the predefined spectrum.

In accordance with another aspect, a method is provided. The method includes collecting patient data by one or more medical body area network (MBAN) devices, transmitting an association request to a hub device on auxiliary channels to associate the one or more MBAN devices with an MBAN system, communicating the collected patient data from the one or more MBAN devices through the MBAN system to the hub device via short-range wireless communication, wherein the communication via short-range wireless communication is within a predefined spectrum, the predefined spectrum being outside the auxiliary channels, and communicating the collected patient data from the hub device to a central monitoring station via longer range wireless communication.

One advantage resides in safe, fast, and power efficient association of MBAN devices with MBAN systems.

Another advantage resides in the reduced or eliminated likelihood of loss of critical medical data acquired by an MBAN system.

Another advantage resides in improved healthcare workflow efficiency, safety, and clinical outcome.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 diagrammatically illustrates a medical body area network (MBAN) system in accordance with the present application.

FIG. 2 diagrammatically illustrates an active channel scan sequence in accordance with the present application.

FIG. 3 diagrammatically illustrates a passive channel scan sequence in accordance with the present application.

FIG. 4 diagrammatically illustrates an orphan scan sequence in accordance with the present application.

FIG. 5 diagrammatically illustrates a beacon based superframe structure in accordance with the present application.

FIG. 6 diagrammatically illustrates an active beacon transmission mode on an auxiliary channel in accordance with the present application.

Figure 7:
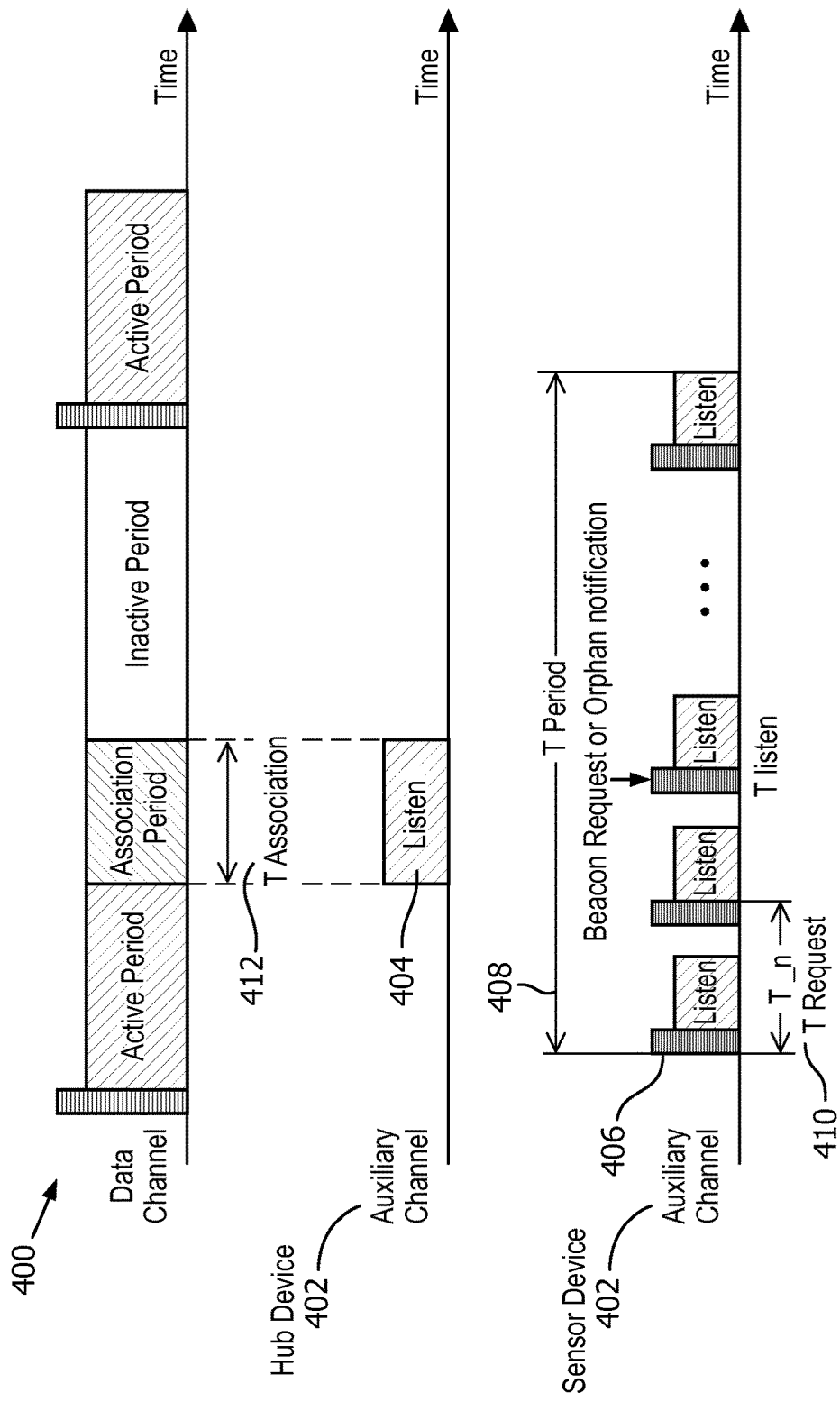

FIG. 7 diagrammatically illustrates an passive beacon transmission mode on an auxiliary channel in accordance with the present application.

Figure 8:
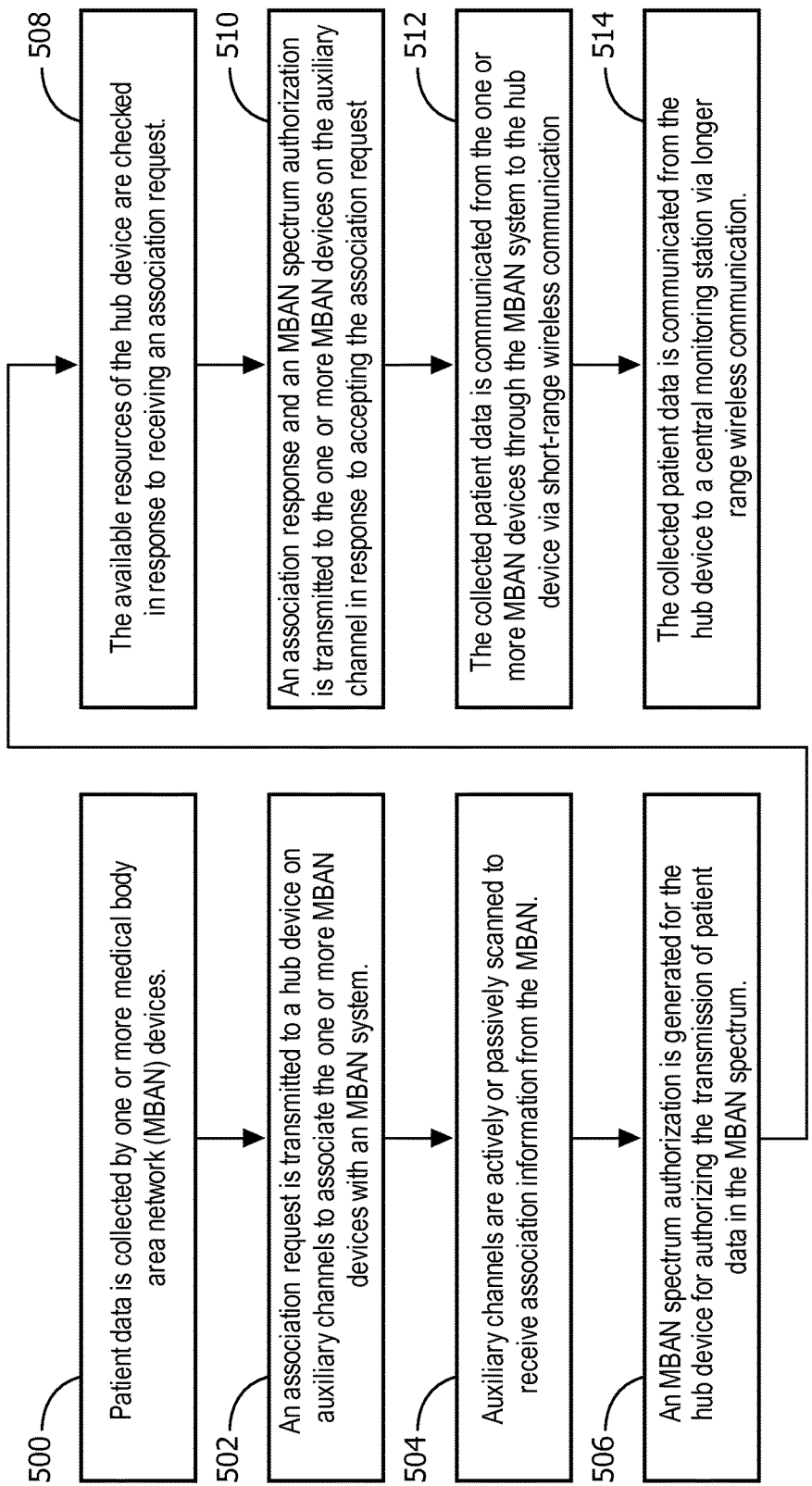

FIG. 8 is a flowchart diagram of the operation of the MBAN system in accordance with the present application.

With reference to FIG. 1, each medical body area networks (MBAN) 10 of a plurality of MBANs includes a plurality of MBAN devices 12, 14 and a corresponding hub device 16. The MBAN devices 12, 14 communicate with the corresponding hub device 16 via a short-range wireless communication protocol. The MBAN 10 is also sometimes referred to in the relevant literature by other equivalent terms, such as a body area network (BAN), a body sensor network (BSN), a personal area network (PAN), a mobile ad hoc network (MANET), or so forth. The term medical body area network (MBAN) 10 is to be understood as encompassing these various alternative terms.

The illustrative MBANs 10 includes two illustrative MBAN devices 12, 14 and a corresponding hub devices 16; however, the number of MBAN devices and hub devices can be one, two, three, four, five, six, or more, and moreover the number of MBAN devices may in some embodiments increase or decrease in an ad hoc fashion as MBAN devices are added or removed from the network to add or remove medical monitoring capability. The MBAN devices 12, 14 include one or more sensors 20 that acquire patient data including physiological parameters such as heart rate, respiration rate, electrocardiographic (ECG) data, or so forth; however, it is also contemplated for one or more of the MBAN devices to perform other functions such as controlled delivery of a therapeutic drug via a skin patch or intravenous connection, performing cardiac pacemaking functionality, or so forth. Other MBAN devices can be associated with a patient, and not all of the above-mentioned MBAN devices have to be associated with a patient at any given time. A single MBAN device may perform one or more functions. The illustrative MBAN devices 12, 14 are disposed on the exterior of an associated patient; however, more generally the MBAN devices may be disposed on the patient, or in the patient (for example, a MBAN device may take the form of an implanted device), or proximate to the patient within the communication range of the short-range communication protocol (for example, a MBAN device may take the form of a device mounted on an intravenous infusion pump (not shown) mounted on a pole that is kept near the patient, and in this case the monitored patient data may include information such as the intravenous fluid flow rate). It is sometimes desirable for the MBAN devices to be made as small as practicable to promote patient comfort, and to be of low complexity to enhance reliability. Accordingly, such MBAN devices 12, 14 are typically low-power devices (to keep the battery or other electrical power supply small) and may have limited on-board data storage or data buffering. As a consequence, the MBAN devices 12, 14 should be in continuous or nearly continuous short-range wireless communication with the corresponding hub device 16 in order to expeditiously convey acquired patient data to the corresponding hub device 16 without overflowing its data buffer.

In FIG. 1, the short-range wireless communication range is diagrammatically indicated by the dotted line used to delineate the MBAN system 10. The short-range wireless communication is typically two-way, so that the MBAN devices 12, 14 can communicate information (e.g., patient data, MBAN device status, or so forth) to the corresponding hub device 16; and the corresponding hub device 16 can communicate information (e.g., commands, control data in the case of a therapeutic MBAN device, or so forth) to the MBAN devices 12, 14. The illustrative hub device is a waist-mounted device which facilitates carrying a longer, heavier battery and other hardware for longer range transmissions; however, the hub device can be otherwise mounted to the patient, for example as a wrist device, adhesively glued device, or so forth. It is also contemplated for the hub device to be mounted elsewhere proximate to the patent, such as being integrated with an intravenous infusion pump (not shown) mounted on a pole that is kept near the patient.

The patient data acquired from the sensors 20 is concurrently transmitted to a controller 22 in the corresponding MBAN device. The MBAN devices 12, 14 serve as a gathering point for the patient data acquired by the sensors 20 and provide temporary storage of the patient data in a memory 24. The MBAN devices 12, 14 also include a communication unit 26 for transmitting the patient data via short-range wireless communication protocol to the corresponding hub device 16. The communication unit 26 include a transceiver (not shown) to transmit the patient data and information, received by the controller 22, and receive information, from the hub device 16.

The short-range wireless communication protocol preferably has a relatively short operational range of a few tens of meters, a few meters, or less, and in some embodiments suitably employs an IEEE 802.15.4 (Zigbee) short-range wireless communication protocol or a variant thereof, or a Bluetooth™ short-range wireless communication protocol or a variant thereof. Although Bluetooth™ and Zigbee are suitable embodiments for the short-range wireless communication, other short-range communication protocols, including proprietary communication protocols, are also contemplated. The short-range communication protocol should have a sufficient range for the hub device 16 to communicate reliably with all MBAN devices 12, 14 of the MBAN system 10. The short-range wireless communication protocol between the MBAN devices 12, 14 and the corresponding hub device 16 and in some embodiments between MBAN devices operate in a frequency spectrum of around 2.3-2.5 GHz.

Due to the strict reliability requirements on MBAN system 10 communications because of the medical content of the patient data being transmitted, an MBAN spectrum is specifically allocated for the communication of the patient data, for example, the 2360-2400 MHz band discussed above. The reliability requirements prohibit the transmission of patient data outside the MBAN spectrum. For example, the MBAN devices 12, 14 are permitted to transmit the acquired patient data to corresponding hub device 16 only when operating in the MBAN spectrum. Being able to operate inside and outside the MBAN spectrum, the MBAN devices 12, 14 are permitted to transmit and receive other data such as MBAN device status data, association data, beacon data, E-key authorization data, and the like outside the MBAN spectrum. For example, when a MBAN device 12, 14 is operating outside the allocated MBAN spectrum, the MBAN devices 12, 14 are permitted to transmit association requests to the corresponding hub device 16 but prohibited to transmit any patient data unless the MBAN device 12, 14 are operating in the allocated MBAN spectrum.

In the MBAN spectrum, the MBAN devices 12, 14 are secondary users of the spectrum. In order to protect primary users, operation of MBAN devices 12, 14 in the MBAN spectrum is prohibited unless the MBAN devices 12, 14 are authorized by an assigned MBAN coordinator 36 or already in an authorized MBAN network. In other words, the MBAN devices 12, 14 can transmit within the MBAN spectrum only when the MBAN device successfully gets authorization from the MBAN coordinator 36 via the corresponding MBAN hub 16. The MBAN coordinator 36 can be a government regulatory entity, the FCC, a regional regulatory entity, the hospital in which the MBAN system is located, and the like. To operate in the MBAN spectrum, the MBAN devices 12, 14, hub device 16, the hospital, or the like need to register with the MBAN coordinator 36. The MBAN coordinator 36 includes a controller 38 for receiving E-key requests and assigning E-keys to authorized MBAN devices. The MBAN coordinator also includes an authorizing unit 40 to determine if it is feasible for a particular MBAN network to use the MBAN spectrum through the coordination with the primary users. If the authorization unit 40 determines that the requesting MBAN devices services can co-exist with the primary users in the MBAN spectrum, the MBAN coordinator generates an E-key for the particular hospital, in the illustrated embodiment, authorizing the use of a portion or all of the MBAN spectrum. For example, a registered healthcare facility will broadcast its E-Key, which is obtained from the MBAN coordinator 36, to each MBAN network that is setup within its facility (indoor). Once an MBAN hub device receives an E-Key from the registered healthcare facility, it will be able to setup and operate an MBAN network within part or the entire of the MBAN spectrum authorized by the E-Key. As long as the MBAN devices 12, 14 are associated with the MBAN hub 16 in the MBAN network, they can communicate with the MBAN hub 16 over the MBAN spectrum. The operation of MBAN devices 12, 14 and the MBAN hub 16 in the MBAN spectrum is also prohibited if the MBAN device 12, 14 are outside a predefined protection zone such as a particular care unit, a healthcare facility, the hospital, and the like. For example, the MBAN devices 12, 14 and MBAN hub 16 can transmit within the MBAN spectrum only when they are located within the predefined protection zone.

The hub device 16 coordinates operation of its MBAN system 10 over the MBAN spectrum to receive the patient data acquired by the sensors 20 of the MBAN devices 12, 14 and transmit the collected patient data from the MBAN 10 via a longer range communication protocol to a central monitoring station 34. The patient data acquired from the sensors 20 is concurrently transmitted from the MBAN devices 12, 14 to a short range communication device 28 in the corresponding hub device 16. The hub device 16 serves as a gathering point for the patient data acquired by the sensors 20 of all the MBAN device 12, 14 in the MBAN network, e.g. all of the MBAN devices associated with one patient, and provides temporary storage of the patient data in a memory 30. The hub device 16 also includes a longer communication unit 32 for transmitting the patient data via a longer range wireless communication protocol to the central monitoring station 34. A controller 33 of the MBAN hub 16 controls communication with the MBAN devices 12, 14, collection and handling of the patient data, retransmission of the patient data to the central monitoring station 34, receiving acknowledgements, setting up the network, associating new MBAN devices, disassociating removed MBAN devices, and the like.

The longer communication unit 32 of the hub device 16 also includes a transceiver which provides the longer-range communication capability to communicate data off the MBAN system 10. In the illustrative example of FIG. 1, the hub device 16 wirelessly communicates with a central monitoring station 34 through a hospital network 42. To provide further illustration, the central monitoring station 34 includes a controller 44 for receiving the patient data from many hub devices. The central monitoring station 34 also includes a display monitor 46 that may, for example, be used to display medical data for the patient that are acquired by the MBAN system 10 and communicated to the central monitoring station 34 via the hospital network 42. The central monitoring station 34 also communicates an electronic patient records sub-system 48 in which patient data and records for all current and past patients is stored. Communication between the central monitoring stations and the patient transmitted/received via the hospital network 42. The longer-range wireless communication is suitably a WiFi communication link conforming with an IEEE 802.11 wireless communication protocol or a variant thereof. However, other wireless communication protocols can be used for the longer-range communication, such as another type of wireless medical telemetry system (WMTS). Moreover, the longer range communication can be a wired communication such as a wired Ethernet link (in which case the hospital networks include at least one cable providing the wired longer range communication link). The longer range communication is longer range as compared with the short-range communication between the MEAN devices 12, 14 and the corresponding hub device 16. For example, the short-range communication range may be of order a meter, a few meters, or at most perhaps a few tens of meters. The longer range communication can be long enough to encompass a substantial portion or all of the hospital or other medical facility whether directly or via a plurality of access points to a hospital network.

The longer-range communication, if wireless, requires more power than the short-range communication—accordingly, the hub device 16 includes a battery or other power source sufficient to operate the longer-range communication transceiver. The hub device 16 also typically includes sufficient on-board storage so that it can buffer a substantial amount of patient data in the event that communication with the hospital network 42 is interrupted for some time interval. In the illustrative case of wireless longer-range communication, it is also to be understood that if the patient moves within the hospital or healthcare facility then the IEEE 802.11 or other wireless communication protocol employed by the hospital network 42 provides for the wireless communication. In this regard, although the patient is typically lying in a bed, more generally it is contemplated for the patient to be ambulatory and to variously move throughout the hospital or healthcare facility. As the patient moves, the MBAN system 10 including the MBAN devices 12, 14 and the hub device 16 moves together with the patient.

In the MBAN 10, the MBAN devices 12, 14 communicate with the hub device 16 via the short-range wireless communication. However, it is also contemplated for various pairs or groups of the MBAN devices 12, 14 to also intercommunicate directly (that is, without using the hub devices 16, 18 as an intermediary) via the short-range wireless communication. This may be useful, for example, to coordinate the activities of two or more MBAN devices in time. Moreover, the hub devices 16, 18 may provide additional functionality—for example, the hub devices 16, 18 may also be a MBAN device that includes one or more sensors for measuring physiological parameters. Still further, while the single hub devices 16, 18 is illustrated, it is contemplated for the coordinating functionality (e.g. data collection from the MBAN devices 12, 14 and offloading of the collected data via the longer range wireless communication) to be embodied by two or more MBAN devices that cooperatively perform the coordinating tasks.

In illustrative FIG. 1, only one MBAN system 10 is illustrated in detail. However, it will be appreciated that more generally the hospital or other medical facility includes a plurality of patients, each having his or her own MBAN system. More generally, the number of MBAN systems may be, by way of some illustrative examples: the hundreds, thousands, tens of thousands, or more depending on the size of the medical facility. Indeed, it is even contemplated for a single patient to have two or more different, independently or cooperatively operating MBAN systems (not illustrated). In this environment, various MBAN systems of different patients can be expected to come into close proximity with one another, such that the ranges of the respective MBAN system short-range wireless communications overlap.

The MBAN devices 12, 14, MBAN hub 16, MBAN system 10, and central monitoring station 34 include at least one processor, for example a microprocessor or other software controlled device configured to execute MBAN software for performing the operations described in further detail below. Typically, the MBAN software is carried on tangible memory or a computer readable medium for execution by the processor. Types of non-transitory computer readable media include memory such as a hard disk drive, CD-ROM, DVD-ROM, internet servers, and the like. Other implementations of the processor are also contemplated. Display controllers, Application Specific Integrated Circuits (ASICs), FPGAs, and microcontrollers are illustrative examples of other types of component which may be implemented to provide functions of the processor. Embodiments may be implemented using software for execution by a processor, hardware, or some combination thereof.

For an unassociated MBAN device to associate with an MBAN 10, the MBAN devices 12, 14 either actively or passively channel scan to receive information about active MBANs 10 nearby. From the received information, the MBAN devices 12, 14 select a desired MBAN 10 to associate with. The MBAN devices 12, 14 switch to the channel currently used by the selected MBAN 10 and send an association request to the hub device 16 of the selected MBAN 10. The hub devices 16 determine whether such association is allowed and send its decision to the MBAN device via an association response. The MBAN device 12, 14 may transmit an acknowledgement frame to the hub device 16 to complete the association procedure. If an associated MBAN device 12, 14 loses its connection to the corresponding hub device 16 it may have to go through a similar procedure to rejoin its MBAN network 10. For example, in the IEEE 802.15.4 std., an orphaned device (i.e. a MBAN device that concludes that it lost connection to the MBAN network may either reset its MAC and redo the association procedure or perform the orphaned device realignment procedure. In the orphaned device realignment procedure, the orphaned device will perform an orphan scan that allows it to attempt to relocate and reconnect to its hub device 16.

In order for the MBAN device 12, 14 to associate or rejoin an MBAN system 10, the MBAN device 12, 14 must communicate with the corresponding hub device 16. But, the MBAN device 12 is not itself authorized to transmit on the MBAN spectrum. Hence, the MBAN device cannot communicate with the hub device 16 on the MBAN spectrum and is required to actively or passively communicate on an auxiliary channel to rejoin or associate to the MBAN system 10. Due to the restrictions of the MBAN spectrum, the MBAN devices 12, 14 are prohibited from transmitting in the MBAN spectrum before receiving authorization through the E-Key from its MBAN hub device. Moreover, during the association procedure and orphan realignment procedure, the MBAN devices 12, 14 have to transmit association request/orphan notification frames before it successfully builds a connection to their corresponding hub device 16 and its identification is verified by the hub device 16 which it will not be allowed to do without having a valid E-key.

To resolve this conundrum, an auxiliary channel outside the MBAN spectrum is used to support MBAN association and orphan association and re-association operations. In the association and orphan alignment procedures, one or plural auxiliary channels are predefined and known to each MBAN devices 12, 14 and the MBAM hub 16. The auxiliary channels are outside the MBAN spectrum and can be used by MBAN devices 12, 14 to transmit information and data without need for E-Key authorization.

To accomplish this, the hub device 16 of each active MBAN 10 operates on two channels: an auxiliary channel and a MBAN channel. All the normal data communications including communication of patient data of an MBAN 10 occur on a MBAN channel within the MBAN spectrum. The auxiliary channel is only used for the association/orphan realignment procedures. To operate on two channels, MBAN devices 12, 14 and hub device 16 may include two radio transceivers: one transmitting on its auxiliary channel and the other transmitting on its MBAN channel. Alternatively, if the MBAN channel and the auxiliary channel are close in frequency a single transmitter/antenna system can be tuned and controlled to switch between the frequencies. The first and second transceivers can have different superframe structures to achieve best power consumption and latency tradeoffs. Alternatively, the MBAN hub device only has single radio that switches between its MBAN channel and auxiliary channel periodically to conduct operations on both channels. The latter option is feasible to MBAN systems since they are low duty-cycle (e.g. <25%) systems and a hub device can switch to another channel for operation during its inactive period for association and re-association operations. When an MBAN hub device 16 initiates its MBAN 10, it picks up an auxiliary channel from a list of auxiliary channels and a MBAN channel for its MBAN operation. The auxiliary channel is only used to support MBAN association/orphan realignment operations. All the data communications including the transmission of patient data between the MBAN hub device 16 and its associated MBAN devices 12, 14 are conducted on the MBAN channel. The MBAN channel and auxiliary channel can be dynamically changed with the dynamic channel selection technique based on clear channel assessment to achieve best performance.

As mentioned above, the MBAN devices 12, 14 either actively or passively channel scan to get receive information about active MBAN networks 10 nearby and select the corresponding MBAN network 10 with which to associate or rejoin. For example, the MBAN devices 12, 14 and the MBAN hub 16 can be assigned to a specific patient and carrying the corresponding patient identifier. As illustrated in FIG. 2, during an active scan, the MBAN device actively transmits a beacon request 100 on each auxiliary channel 102, 104, 106 and listen on that channel for a predefined period 108 for responses (e.g. beacon frames) from the hub device 16 on the channel. Through the received beacon frames, the MBAN device determines which MBAN networks 10 are working on the current channel and other information about those networks. Based on the received responses, the MBAN device chooses to which MBAN networks 10 to connect, e.g. the hub with the same patient identifier.

As illustrated in FIG. 3, during a passive scan, the MBAN device listens on each auxiliary channel 120, 122, 124 for predefined period 126 trying to receive beacon frames from the hub devices currently working on such channel.

As illustrated in FIG. 4, during an orphan scan, the orphaned MBAN device actively transmits an orphan notification command 140 on each auxiliary channel 142, 144, 146 and listens to the channel for a predefined period 148 trying to get a response from its hub device. Once the orphaned device receives a coordinator realignment command (response) from the targeted hub device, it will stop its orphan scan and start to realign with the targeted hub device.

As mentioned above, the beacons are based on a superframe structure. With reference to FIG. 5, a superframe structure is illustrated. The superframe 200 includes three portions: an active period 202 in which the hub device and its MBAN devices communicate with each other on the data channel; an association period 204 in which the hub device switches to its auxiliary channel for possible association/orphan realignment operations and its MBAN devices are inactive (e.g. in sleep mode); and an inactive period 206 in which both the hub device and its MBAN devices are inactive.

With reference to FIG. 6, an active beacon transmission mode 300 on the auxiliary channel is illustrated. In this mode, the hub device of an active MBAN network periodically transmits its beacon frame 302 in the association period 304 on its auxiliary channel 306. After its beacon transmission, the hub device switches to the listen mode 308 trying to receive possible association requests from MBAN devices. If a MBAN device wants to associate to a MBAN, it passively scans the auxiliary channels. Specifically, the MBAN device switchs to each auxiliary channel 306 and listens on that channel for a period 310 of $T_{listen}$, which is no less than the superframe length to guarantee that the MBAN device can hear a beacon frame 302 from a hub device.

Once the MBAN device receives the beacon frame 302 from its desired hub device, it stops listening and stop performing the channel scan operation. The MBAN device then transmits an association request to the desired hub device on the current auxiliary channel 306 within the listen period of the hub device. If the hub device receives the association request correctly, it verifies the MBAN device identification, checks its available resource and makes decision whether to accept the association request. The hub device sends it decision to the MBAN device through the auxiliary channel 306. If the association request is accepted, the hub device also delivers a valid E-Key to the MBAN device. Once the association is completed and the MBAN device successfully associates to the desired network, it switches to the data channel of that network and perform further communications over the data channel. Once the MBAN device receives a valid E-Key, it can transmit in part or all of the MBAN spectrum that is enabled by the E-Key.

If an associated MABN device loses its connection to its hub device and becomes an orphaned device, its E-key becomes invalid and the orphan MBAN device initiates an orphan device realignment procedure to reconnect to the hub device. First, the orphan device switches to its auxiliary channel (the one used before its disconnection) trying to obtain a beacon frame from its hub device there. Since the orphan device associated to the network before its disconnection, it has information about the auxiliary channel used by that network and the timing of beacon transmission on that auxiliary channel and this information can be utilized by the orphan device to do realignment (e.g., when to switch to the auxiliary channel to receive beacons). Once it receives a beacon from its hub device, it sends an orphan notification to its hub device on the auxiliary channel. The hub device then replies to it with an orphan realignment command and a valid E-Key to the orphan device. The orphan device then completes its realignment by switching back to its data channel and realigning with the hub device. If the orphan device has some important data to transmit, it notifies the hub device using the orphan notification. The hub device allows such transmission through its orphan realignment command. If allowed, the MBAN device can start transmission on its auxiliary channel right after it receives the orphan realignment command from the hub device. This ensures timely delivery of important data from the orphan device to the hub device.

It is possible that during the period that an orphan device loses connection to its hub device, the hub device may change its auxiliary channel to another one. So if the orphan device does not receive any response (orphan realignment command from its hub device) within a predefined period, it does orphan scan on other auxiliary channels. The hub device broadcasts to its slave device an ordered list of auxiliary channels that it may use. The orphan device does the orphan scan based on the ordered list to reduce the realignment time.

With reference to FIG. 7, a passive listen mode 400 on the auxiliary channel is illustrated. In this mode, there is no active beacon transmission from the hub device on its auxiliary channel 402. Instead, the hub device of an active MBAN network periodically listens on its auxiliary channel in an association period 404.

If a MBAN device wants to associate to a MBAN network, it actively scans the auxiliary channels. Specifically, the MBAN device switches to each auxiliary channel and transmits a series of beacon request frames 406 on that channel. After each beacon request transmission 406, it listens to the channel for a predefined time trying to receive responses from the hub devices working on that auxiliary channel. The MBAN device repeats such operation on an auxiliary channel 402 for a time period of $T_{period}$ 408, which is at least no less than the superframe length. The interval between two beacon request transmissions, $T_{Request}$ 410, is no larger than an association period $T_{Association}$ 412 to guarantee that a hub device gets chances to hear at least one beacon request 406. Once a hub device receives a beacon request 406 from a MBAN device, it responds with a beacon transmission within a predefined time. The MBAN device then will be able to detect those beacon responses. If the MBAN device receives a beacon from its desired hub device, it stops beacon request transmissions and also active scan operation. It sends an association request on the current auxiliary channel 402 to the selected hub device. If the hub device receives the association request correctly, it verifies the MBAN device identification, checks its available resource and makes a decision whether to accept the association request. The hub device sends its decision to the MBAN device through the auxiliary channel 402. If the association request is accepted, the hub device also delivers a valid E-Key to the MBAN device. Once the association is completed and the MBAN device successfully associates to the desired network, it switches to the data channel of that network and perform further communications over the data channel. Since the MBAN device already has a valid E-Key, it can transmit in part or all of the MBAN spectrum that is enabled by the E-Key.

Since the events of device association/realignment would be not frequent in real applications, the traffic of an auxiliary channel would be very limited. Therefore, several MBAN networks can share a same auxiliary channel and much fewer auxiliary channels (compared to data channels) are needed to support MBAN coexistence. Usually one or two auxiliary channels would be enough. During device association, there are much fewer channels need to be scanned by a sensor device. This can speed up association/realignment operations and reduce power consumption of sensor devices.

FIG. 8 illustrates the operation of the MBAN system. In a step 500, patient data is collected by one or more medical body area network (MBAN) devices. In a step 502, an association request is transmitted to a hub device on auxiliary channels to associate the one or more MBAN devices with an MBAN system. In a step 504, auxiliary channels are actively or passively scanned to receive association information from the MBAN. In a step 506, an MBAN spectrum authorization is generated for the hub device for authorizing the transmission of patient data in the MBAN spectrum. In a step 508, the available resources of the hub device are checked in response to receiving an association request. In a step 510, an association response and an MBAN spectrum authorization is transmitted to the one or more MBAN devices on the auxiliary channel in response to accepting the association request. In a step 512, the collected patient data is communicated from the one or more MBAN devices through the MBAN system to the hub device via short-range wireless communication, the communication via short-range wireless communication within a predefined spectrum and the predefined spectrum being outside the auxiliary channels. In a step 514, the collected patient data is communicated from the hub device to a central monitoring station via longer range wireless communication.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A medical system comprising:
   one or more medical body area network (MBAN) systems, each MBAN system including:
      one or more MBAN devices configured to acquire and communicate patient data with a hub device via short-range wireless communication, the communication of the patient data via the short-range wireless communication being within a predefined MBAN spectrum, the MBAN system being a secondary user in the predefined MBAN spectrum;
      the hub device being configured to receive patient data communicated from the one or more MBAN devices via the short-range wireless communication and communicate with a central monitoring station via a longer range communication
   wherein the one or more MBAN devices are configured to transmit an association request to the hub device via the short-range wireless communication on one or more auxiliary channels to associate each MBAN device with the hub device, the auxiliary channels being outside the predefined MBAN spectrum.

2. The medical system according to claim 1, further including:
   a MBAN coordinator configured to generate MBAN spectrum authorizations for the one or more hub devices to authorize the transmission of patient data in the MBAN spectrum, each hub device authorized for the transmission of patient data in the MBAN spectrum being configured to respond to the association request from a new MBAN device by issuing the new MBAN device a key which enables the new MBAN device to communicate patient data in the MBAN spectrum.

3. The medical system according to claim 1, wherein the one or more MBAN devices actively or passively scan the auxiliary channels to receive information about the one or more MBAN systems, the information including the resources available of the one or more MBAN systems.

4. The medical system according to claim 1, wherein in response to receiving an association request, the hub device is configured to check its available resources to determine whether to accept the association request and if resources are available, issues a key to the MBAN device requesting association to enable the MBAN device to communicate in the MBAN spectrum.

5. The medical system according to claim 1, wherein the hub device transmits an association response and MBAN spectrum authorization to the one or more MBAN devices on the auxiliary channel in response to accepting the association request.

6. The medical system according to claim 1, wherein the MBAN spectrum are within the 2360 MHz-2390 MHz range and the auxiliary channels are outside the MBAN spectrum.

7. The medical system according to claim 1, wherein each MBAN device has a single transceiver configured to transmit and receive the short-range wireless communications in the MBAN spectrum and on the auxiliary channels and each hub device has a single transceiver configured to transmit and receive the short-range wireless communications in the MBAN spectrum and on the auxiliary channels.

8. The medical system according to claim 7, wherein an MBAN spectrum protocol and an auxiliary channel protocol include superframe structures, the superframe structures include at least one of:
   an active period in which the hub device and the one or more MBAN devices communicate with each other on the MBAN spectrum;
   an association period in which the hub device switches to the auxiliary channels for possible association operations; and
   an inactive period in which both the hub device and MBAN devices are in an inactive state.

9. The medical system according to claim 1, wherein the hub device includes an active transmission mode in which the hub device periodically transmit a beacon frames in the association period on the auxiliary channels and periodically listen to receive association requests from the one or more MBAN devices.

10. The medical system according to claim 1, wherein the hub device include an passive transmission mode in which the hub device periodically listen to receive association requests from the one or more MBAN devices.

11. A method comprising:
    collecting patient data by one or more medical body area network (MBAN) devices;
    transmitting an association request to a hub device via short-range wireless communication on auxiliary channels to associate the one or more MBAN devices with an MBAN system;
    transmitting a key from the hub device to the one or more association requesting MBAN devices, the key authorizing the one or more MBAN devices to communicate with the hub device on at least a portion of a predefined MBAN spectrum;
    communicating the collected patient data using the key from the one or more MBAN devices to the hub device via short-range wireless communication, in the authorized portion of the predefined MBAN spectrum, the predefined MBAN spectrum being outside the auxiliary channels; and
    communicating the collected patient data from the hub device to a central monitoring station via longer range wireless communication.

12. The method according to claim 11, further including:
    with an MBAN coordinator remote from the MBAN system, generating the MBAN spectrum authorization key for the hub device for authorizing the transmission of patient data in at least the portions of the MBAN spectrum.

13. The method according to claim 11, further including:
    actively or passively scanning auxiliary channels to receive associations information from the MBAN.

14. The method according to claim 11, further including:
with a common transceiver, transmitting both the association request from the one or more MBAN devices to the hub device on one of the auxiliary channels to associate with the MBAN and the patient data in the MBAN spectrum.

15. The method according to claim 11, wherein the MBAN spectrum is within a 2360 MHz-2390 MHz range and the auxiliary channels are outside the MBAN spectrum and in a range of 2300 MHz-2360 MHz and 2390 MHz-2500 MHz.

16. The method according to claim 11, further including:
checking the available resources of the hub device in response to receiving an association request; and
transmitting an association response and an MBAN spectrum authorization to the one or more MBAN devices on the auxiliary channel in response to accepting the association request.

17. The method according to claim 11, wherein a MBAN spectrum protocol and an auxiliary channel protocol include superframe structures, the superframe structures including at least one of:
an active period in which the hub device and the one or more MBAN devices communicate with each other on the MBAN spectrum;
an association period in which the hub device switches to the auxiliary channels for possible association operations; and
an inactive period in which both the hub device and MBAN devices are in an inactive state.

18. A medical system comprising:
one or more processors programmed to perform a method according to claim 11.

19. A non-transitory computer readable medium containing software which when loaded into processor programs the processor to perform a method according to claim 11.

* * * * *